United States Patent [19]
DeRoche

[11] Patent Number: 5,484,395
[45] Date of Patent: Jan. 16, 1996

[54] FIREMAN'S BACK BRACE

[76] Inventor: William P. DeRoche, 3564 Tiffany La., Shoreview, Minn. 55126

[21] Appl. No.: 295,408

[22] Filed: Aug. 25, 1994

[51] Int. Cl.⁶ ................................................. A61F 5/00
[52] U.S. Cl. ........................... 602/19; 2/311; 2/312; 128/96.1; 128/100.1; 128/101.1; 128/106.1
[58] Field of Search ..................... 602/19, 20; 2/108, 2/338, 311, 312, 304, 320; 128/D15

[56] References Cited

U.S. PATENT DOCUMENTS

| | | | |
|---|---|---|---|
| 4,095,415 | 6/1978 | Bower | 2/338 |
| 4,833,730 | 5/1989 | Nelson | 602/19 X |
| 5,040,524 | 8/1991 | Votel et al. | 602/19 |
| 5,046,488 | 9/1991 | Schiek, Sr. | 602/19 |
| 5,081,719 | 1/1992 | Donnelly | 2/311 |
| 5,179,942 | 1/1993 | Drulias et al. | 602/19 X |
| 5,334,134 | 8/1994 | Saunders | 602/19 |
| 5,351,340 | 10/1994 | Aldridge | 2/108 |

OTHER PUBLICATIONS

Valeo™, Golf Day Product Brochure, Catalog 117B, p. 17.

Primary Examiner—Richard J. Apley
Assistant Examiner—Kim M. Lee

[57] ABSTRACT

A fireman's back brace including a lumbar spinal support belt disposed about a user's torso by a first coacting fastening means, a straplike tensioning member pair affixed to the lumbar spinal support belt and being wrappedly secured about the user's torso using a second coacting fastening means, manual engagement loops affixed to free ends of the straplike tensioning member pair, and a releasable means for affixing the fireman's back brace to existing garmentlike firefighting equipment. The fireman's back brace is composed of flame retardant materials.

1 Claim, 4 Drawing Sheets

FIREMAN'S BACK BRACE

BACKGROUND OF THE INVENTION

1. Field of the Invention

The present invention relates to back braces and fireman's appliances and more particularly pertains to a fireman's back brace which may be employed to provide support of a firefighter's back during lifting.

2. Description of the Prior Art

The use of back braces is known in the prior art. More specifically, back braces heretofore devised and utilized for providing support of a lower back during lifting are known to consist basically of familiar, expected and obvious structural configurations, notwithstanding the myriad of designs encompassed by the crowded prior art which have been developed for the fulfillment of countless objectives and requirements.

The present invention is directed to improving devices for a fireman's back brace in a manner which is safe, secure, economical and aesthetically pleasing.

For example, U.S. Pat. No. 5,267,947 to James et al. discloses a contour lumbar support comprising a belt supporting the lumbar region of the spine providing transverse and axial support to hard tissues thereof. The James et al. invention comprises an incrementally adjustable belt having a contoured lumbar spinal support portion and has no antistatic and flame retardant properties. The present invention comprises a continuously adjustable lumbar support belt having antistatic and flame retardant properties and furthermore is waterproof and susceptible to manual adjustment by gloved hands.

In U.S. Pat. No. 4,026,547 to Silverstolpe et al. a belt with adjustable back support plate is disclosed for use by sailors providing support when inclined outward from a vessel, particularly a racing vessel for counterbalancing vessel inclination. The Silverstolpe et al. invention comprises a cooperating series of portions extending around crotch, waist, back, and over shoulders of a user and has a front located hook device and a back support plate. The Silverstolpe et al. invention is employed for use aboard a sailing vessel and is unsuited for use by active firefighters to reduce back stresses during lifting because of a lack of localized lumbar spinal support and an insusceptibility to rapid donning as required for all firefighting worn equipments. The present invention is designed for use by firefighters and has no requirement for engaging lines as used on shipboard. The present invention additionally is composed of flame retardant materials and is detachably affixed to other portions of a fireman's worn equipments and requires no engagement with body portions other than the back and waist thereby providing rapid donning along with other members of a firefighter's worn equipment.

In U.S. Pat. No. 5,129,105 to Kleinman a fireman's suspenders with padding and fire-resistant inelastic construction is described comprising a pair of suspenders and a belt. wherein the suspenders pair is substantially inelastic and thereby insusceptible to stretching, and more particularly insusceptible to stretching beyond an elastic limit. There is no provision in the Kleinman invention for supporting the back of a user thereof. The present invention is not employed as suspension for any worn article and furthermore is devised to support the lumbar spine of a firefighter to mitigate hazards to a user's back during lifting.

In U.S. Pat. No. 5,147,261 to Smith et al. a lifting belt is disclosed for supporting the lower fifth lumbar region of the back during lifting. The Smith et al. invention comprises a detachable lumbar belt and an elastic abdominal belt joining at a lumbar compression pad. A disadvantage in this prior art lies in a lack of use of fire retardant construction therein, a lack of provision for adjusting the support belt with gloved hands, and a lack of provision for rapidly donning the support belt in conjunction with firefighter dress ensembles. The present invention is of flame retardant composition and is fully adjustable using gloved hands. The present invention additionally is detachably affixed to a member of the firefighter's dress ensemble thereby permitting rapid donning of an entire worn equipment complement including the present invention.

U.S. Pat. No. 5,046,488 to Schiek Sr. discloses a support belt for the lumbar vertebrae. The disclosure teaches a lumbar vertebrae support belt encircling an abdominal region. The disclosure makes no provision for adjustability using heavily gloved hands. Furthermore, there are no provisions for flame retardancy. There is no teaching to detachably affix the invention to existing worn firefighter clothing. The present invention comprises a flame retardant belt supporting the spinal vertebrae and furthermore being adjustable by heavily gloved hands. The present invention is also detachably affixable to fireman's clothing using hook and loop fasteners or snap engagement.

In this respect, the fireman's back brace according to the present invention substantially departs from the conventional concepts and designs of the prior art, and in so doing provides an apparatus primarily developed for the purpose of providing adjustable lumbar spinal support for firemen.

Therefore, it can be appreciated that there exists a continuing need for new and improved fireman's back brace which can be employed by an active firemen to limit back stress during lifting of heavy objects encountered in the course of firefighting operations. In this regard, the present invention substantially fulfills this need.

As illustrated by the background art, efforts are continuously being made in an attempt to improve lumbar spine support belts. No prior effort, however, provides the benefits attendant with the present invention. Additionally, the prior patents and commercial techniques do not suggest the present inventive combination of component elements arranged and configured as disclosed and claimed herein.

The present invention achieves its intended purposes, objects, and advantages through a new, useful and unobvious combination of method steps and component elements, with the use of a minimum number of functioning parts, at a reasonable cost to manufacture, and by employing only readily available materials.

SUMMARY OF THE INVENTION

In view of the foregoing disadvantages inherent in the known types of lumbar spine support belts now present in the prior art, the present invention provides an improved fireman's back brace construction wherein the same can be utilized for providing lumbar spinal support for a fireman performing firefighting duties. As such, the general purpose of the present invention, which will be described subsequently in greater detail, is to provide a new and improved fireman's back brace apparatus and method which has all the advantages of the prior art lumbar spinal support belts and none of the disadvantages.

The invention is defined by the appended claims with the specific embodiment shown in the attached drawings. For the purpose of summarizing the invention, the invention may be incorporated into an inelastic adjustable lumbar support belt having a pair of adjustable tensioning straplike members affixed thereto. The lumbar support belt is adjustably closed upon itself using hook and loop fasteners. The tensioning straplike members are of elastic composition and are fastened to the lumbar support belt at a first end pair thereof and are detachably closed upon each other at a second end pair thereof.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. In as much as the foregoing has outlined rather broadly the more pertinent and important features of the present invention in order that the detailed description of the invention that follows may be better understood so that the present contribution to the art can be more fully appreciated. Additional features of the invention will be described hereinafter which form the subject of the claims of the invention. It should be appreciated by those skilled in the art that the conception and the disclosed specific methods and structures may be readily utilized as a basis for modifying or designing other structures for carrying out the same purposes of the present invention. It should be realized by those skilled in the art that such equivalent methods and structures do not depart from the spirit and scope of the invention as set forth in the appended claims.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

Therefore, it is an object of the present invention to provide an improved fireman's back brace being of nonflammable construction and of specific utility to firefighting usage.

It is therefore an additional object of the present invention to provide a new and improved fireman's back brace which has all the advantages of the prior art backbraces and lumbar spinal support belts and none of the disadvantages.

It is another object of the present invention to provide a new and improved fireman's back brace which may be easily and efficiently manufactured and marketed.

It is a further object of the present invention to provide a new and improved fireman's back brace which is of a durable and reliable construction.

An even further object of the present invention is to provide a new and improved fireman's back brace which is susceptible of a low cost of manufacture with regard to both materials and labor, and which accordingly is then susceptible of low prices of sale to the consuming public, thereby making such fireman's back braces economically available to the buying public.

Still yet another object of the present invention is to provide a new and improved fireman's back brace which provides in the apparatuses and methods of the prior art some of the advantages thereof, while simultaneously overcoming some of the disadvantages normally associated therewith.

Still another object of the present invention is to provide a new and improved fireman's back brace detachably affixable to existing fireman's worn gear.

Yet another object of the present invention is to provide a new and improved fireman's back brace susceptible to manual adjustment under field conditions using heavily gloved hands.

Even still another object of the present invention is to provide a new and improved fireman's back brace of nonflammable composition.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention. The foregoing has outlined some of the more pertinent objects of this invention. These objects should be construed to be merely illustrative of some of the more prominent features and applications of the present invention. Many other beneficial results can be attained by applying the disclosed invention in a different manner or by modifying the invention within the scope of the disclosure. Accordingly, other objects and a fuller understanding of the invention may be had by referring to the summary of the invention and the detailed description of the preferred embodiment in addition to the scope of the invention defined by the claims taken in conjunction with the accompanying drawings.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
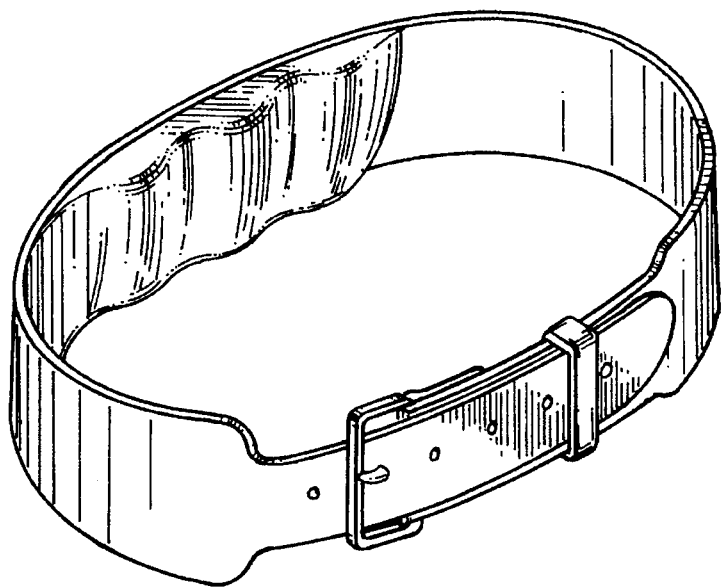
FIG. 1 is prior art.
Figure 2:
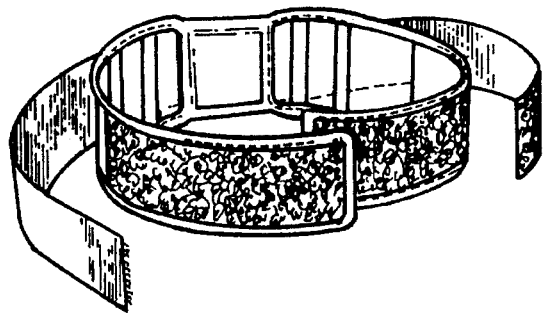
FIG. 2 is prior art.
Figure 3:
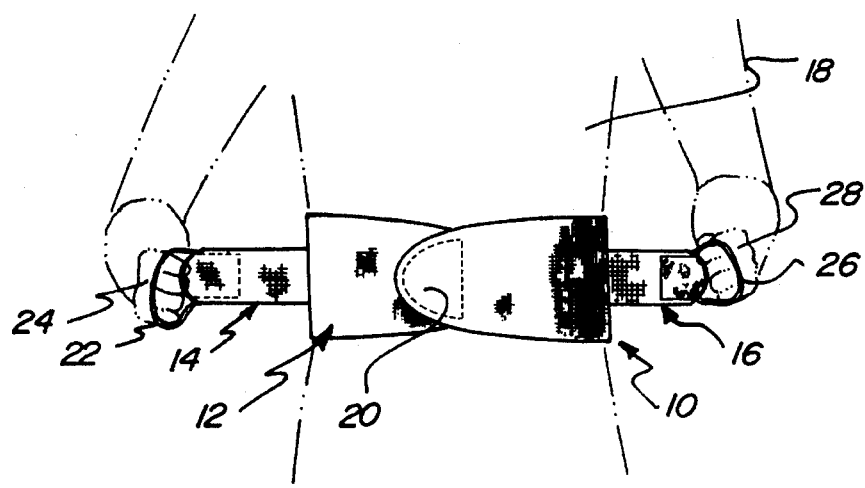
FIG. 3 is a side elevational view of the fireman's back brace showing a disposition on a human user during adjustment.

With reference now to the drawings, and in particular to FIG. 3 thereof, a new and improved fireman's back brace embodying the principles and concepts of the present invention and generally designated by the reference numeral 10 will be described.

Figure 4:
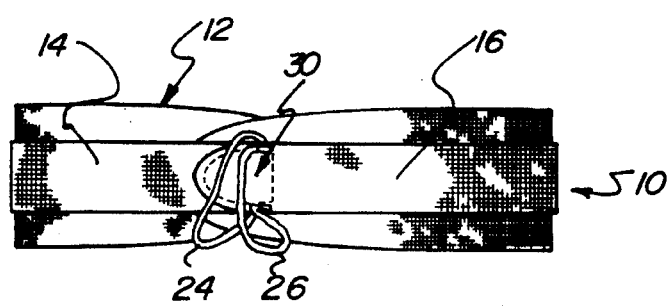
FIG. 4 is a side elevational view of the fireman's back brace in an adjusted position.

From an overview standpoint, the fireman's back brace 10 is adapted for use by a human firefighter and garmentlike equipment said firefighter may wear. See FIG. 3. The fireman's back brace 10 comprises a lumbar support belt 12 having a first straplike tensioning member 14 and a second straplike tensioning member 16 affixed thereto. Lumbar support belt 12 is detachably affixed to a human wearer 18 by first coacting fastener. First straplike tensioning member 14 is manually adjusted to provide requisite lumbar spinal support by grasping first pull loop 22 with hand 24 and stretching the first straplike tensioning member 14 across a front portion of human 18. Second straplike tensioning member 16 is likewise manually adjusted to provide requisite lumbar spinal support by grasping second pull loop 26 with hand 28 and stretching the second straplike tensioning member 16 across a front portion of human 18. First and second straplike tensioning members 14 and 16 are maintained at a particular tension by engagement of second coacting fastener 30. See FIG. 4. A third coacting fastener may be employed to detachably affix the fireman's back brace 10 to garmentlike items of a fireman's equipment.

Figure 5:
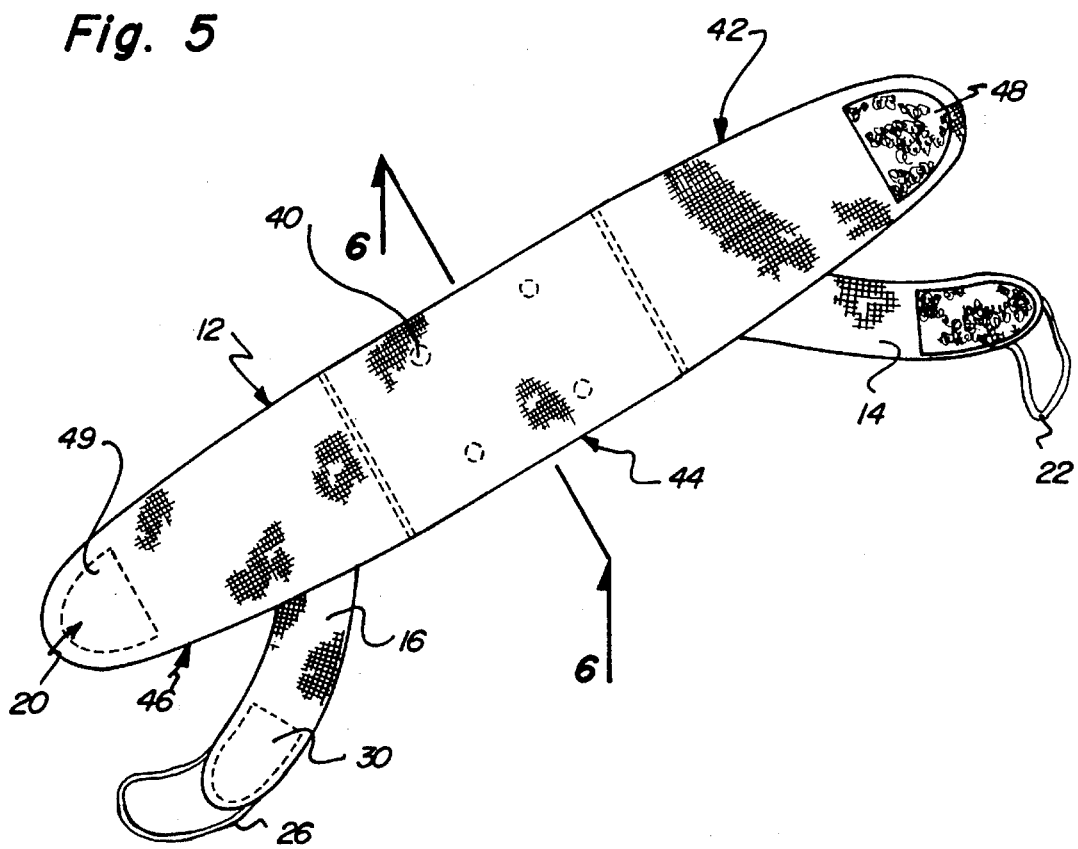
FIG. 5 is a side elevational view of a fireman's back brace showing an outer surface.

More specifically, it will be noted that the fireman's back brace 10 comprises a substantially inelastic enwidened lumbar support belt 12 adjustably closed by first coacting fastener 20, first and second elastic straplike tensioning members 14 and 16 adjustably interconnecting by second coacting fastener 30, first and second pull loops 24 and 26, and a third coacting fastener 40. See FIG. 5. Lumbar support belt 12 is of woven composition and may comprise one or more layers bonded or sewn to form a singular unit. Lumbar support belt 12 comprises a first end portion 42, a central portion 44, and a second end portion 46. First end portion 42 comprises a smoothly curving termination of a free end thereof and a pile portion 48 of coacting fastener 20.

Figure 6:
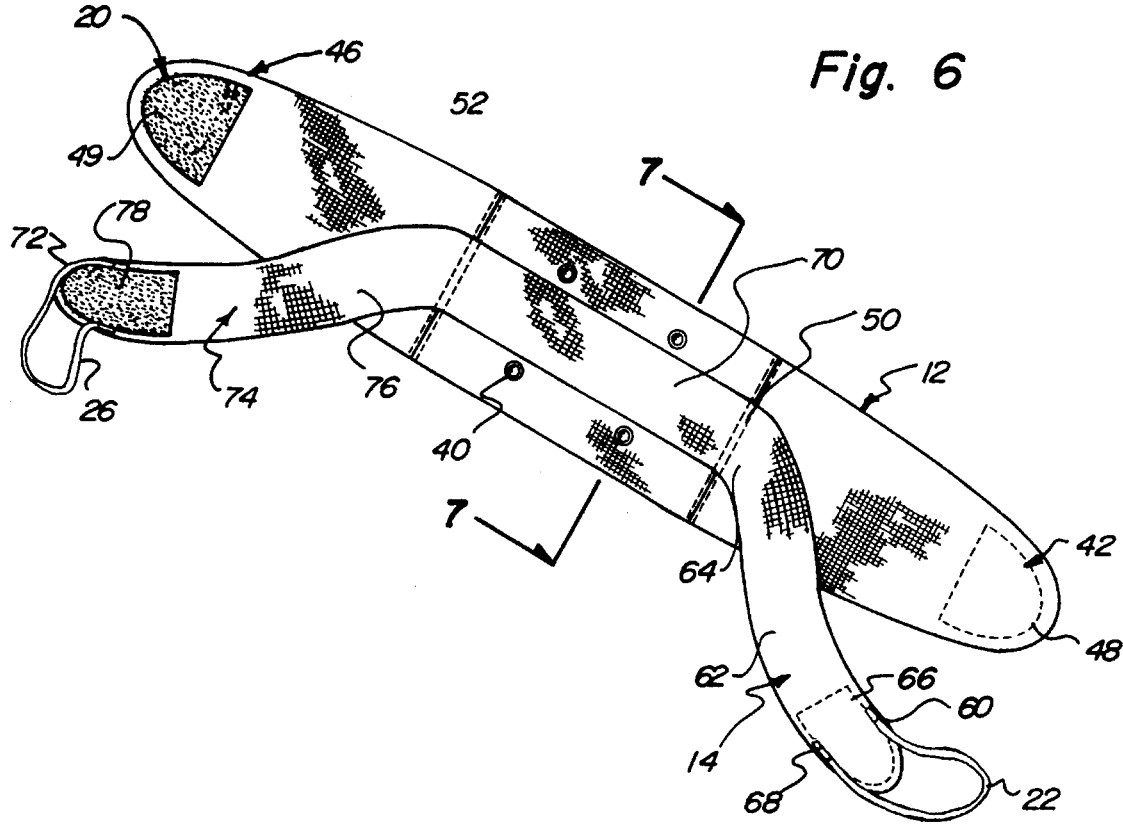
FIG. 6 is a side sectional view of a fireman's back brace taken substantially upon the plane indicated by the section line 6—6 of FIG. 5.
Figure 7:
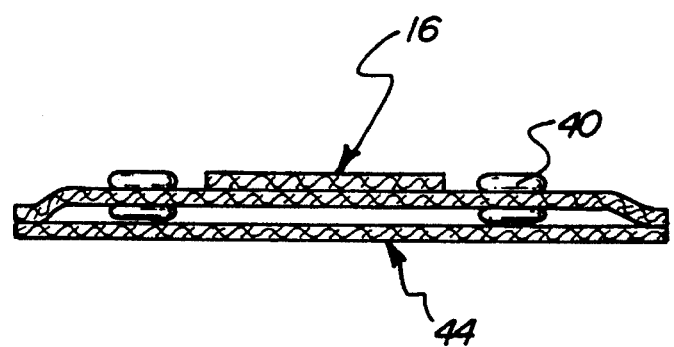
FIG. 7 is a side sectional view of a fireman's back brace taken substantially upon the plane indicated by the section line 7—7 of FIG. 6.

Central portion 44 engages a lumbar spinal portion of human 18 and may have disposed thereupon one or more lumbar engagement pads, or comprise a simple planar beltlike-engagement region. Central portion 44 comprises an enwidened section having substantially parallel or slightly curveate free edges and third coacting fastener 40 affixed thereon and furthermore first and second straplike tensioning members 14 and 16 are fastened thereto at first seam 50 and second seam 52. See FIGS. 6 and 7. First seam 50 and second seam 52 are sewn or otherwise bonded joints capable of withstanding forces encountered during adjustable disposition upon a human 18 wearer. Second end portion 46 comprises a smoothly curving termination of a free end thereof and a plurality of tiny hooklike members disposed in a group and forming a hooking portion 49 of coacting fastener 20.

First straplike tensioning member 14 comprises a first end portion 60, a central portion 62, and a second end portion 64. First end portion 60 comprises a smoothly curving free end termination and a pile portion 66 of coacting fastener 30. Additionally, pull loop 22 is affixed to first end portion 60 using sewn or bonded fastening 68. Central portion 62 comprises an elongated straplike portion of elastic material having substantially parallel free edges thereof. Second end portion 64 comprises a sewn or bonded seam 50 termination wherein second end portion 64 may continue past seam 50 to form a continuous interface portion 70 of first straplike tensioning member 14 and second straplike tensioning member 16.

Second straplike tensioning member 16 comprises a first end portion 72, a central portion 74, and a second end portion 76. First end portion 72 comprises a smoothly curving free end termination and a plurality of tiny hooklike members disposed in a group and forming a hooking portion 78 of coacting fastener 30. Additionally, pull loop 26 is affixed to first end portion 72 using sewn or bonded fastening 80. Central portion 74 comprises an elongated straplike portion of elastic material having substantially parallel free edges thereof. Second end portion 76 comprises a sewn or bonded seam 52 termination wherein second end portion 76 may continue past seam 52 to form a continuous interface portion 70 of first straplike tensioning member 14 and second straplike tensioning member 16.

Third coacting fastener 40 comprises a plurality of first snaplike members engaging a plurality of opposing gender snaplike members affixed to outer wear of human 18 whereby the fireman's back brace 10 may be detachably affixed to fireman's worn equipment.

Figure 8:
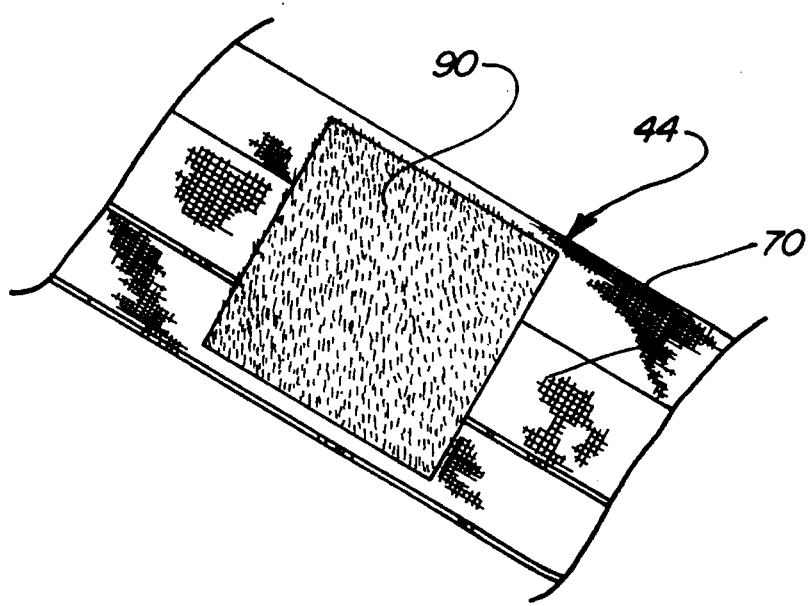
FIG. 8 is a fragmentary perspective view of a fireman's back brace showing a coacting fastening pad.

In an alternate embodiment, third coacting fastener 40 comprises a section 90 having a plurality of tiny hooklike members disposed thereon wherein section 90 engages a pile section fastened to an inner portion of outer wear of human 18. See FIG. 8.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention. In as much as the present disclosure includes that contained in the appended claims as well as that of the foregoing description. Although this invention has been described in its preferred forms with a certain degree of particularity, it is understood that the present disclosure of the preferred form has been made only by way of example and numerous changes in the details of construction and combination and arrangement of parts may be resorted to without departing from the spirit and scope of the invention.

What is claimed as being new and desired to be protected by Letters Patent of the United States is as follows:

1. A new and improved fireman's back brace for adjustably supporting a lumbar spine portion of a firefighter's back comprising:

a lumbar spinal support belt having an exterior surface, an interior surface, and a strap tensioning member affixed to said exterior surface to provide adjustable tension thereto, said lumbar spinal support belt comprises an inelastic wide band member having a first end portion, a central portion, and a second end portion wherein said first end portion is a free end having a first portion of a support belt co-acting fastener disposed thereupon, said central portion has a means for fastening said strap tensioning member thereto, and second end portion is a free end having a second portion o a support belt co-acting fastener disposed thereupon, said strap tensioning member comprises and elastic material having a co-acting fastener for releasably attaching each said free end together;

manual engagement means for each free end of said strap tensioning member, said manual engagement member comprises a cord material forming a loop permanently fastened at each end of the free ends of said strap tensioning member; and fastening means in fixed association to said lumbar spinal support belt for detachably affixing said fireman's back brace to a portion of a fireman's garment worn equipment.

* * * * *